Figure 1:
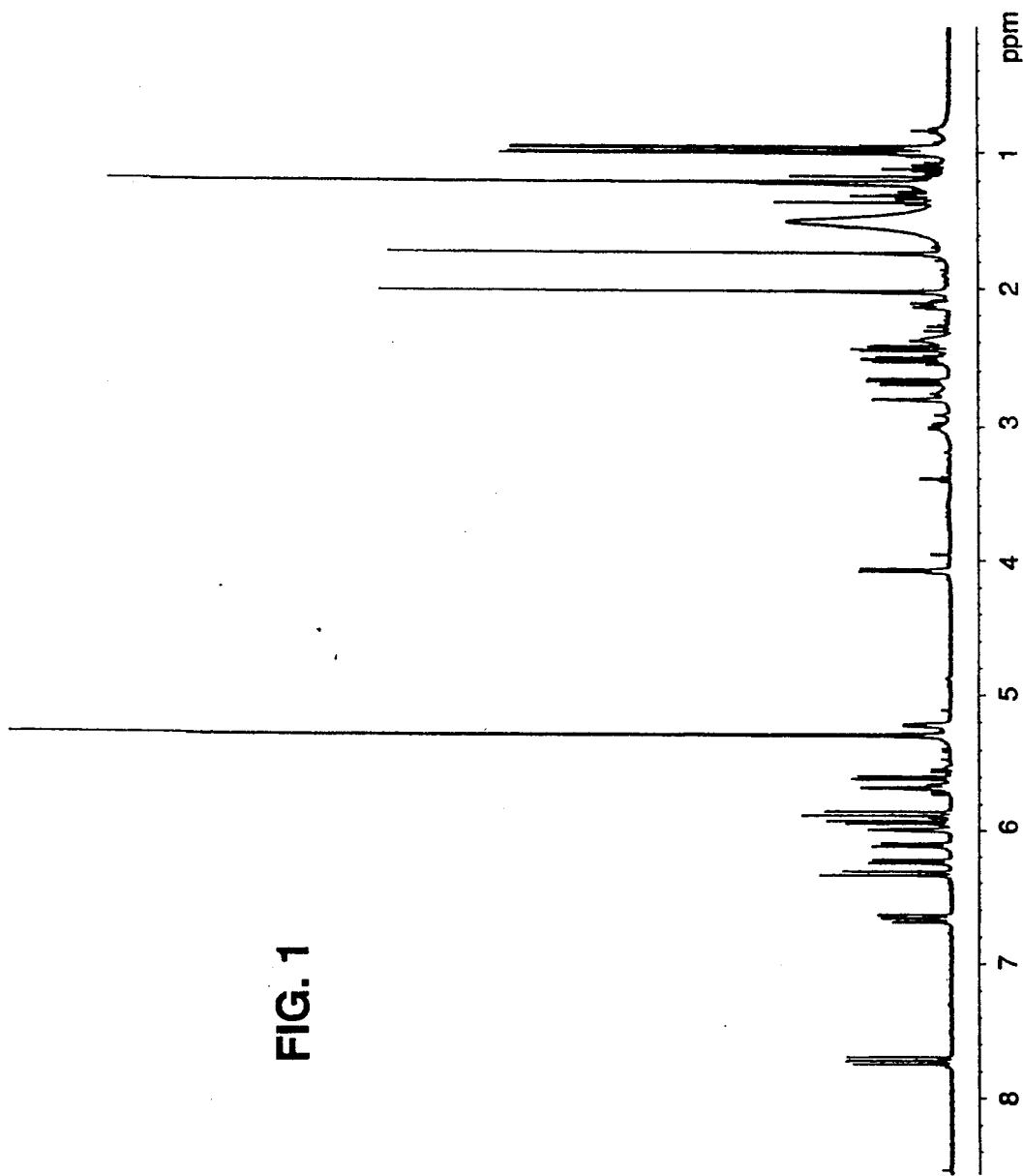

United States Patent [19]

Bartizal et al.

[11] Patent Number: 5,166,217
[45] Date of Patent: Nov. 24, 1992

[54] ANTIFUNGAL AGENTS

[75] Inventors: Kenneth F. Bartizal, Somerset; Walter Rozdilsky, Clifford Beach; Wendy S. Horn, Westfield, all of N.J.

[73] Assignee: Merck & Co., Inc., Rahway, N.J.

[21] Appl. No.: 798,378

[22] Filed: Nov. 26, 1991

Related U.S. Application Data

[63] Continuation-in-part of Ser. No. 670,638, Mar. 18, 1991, abandoned.

[51] Int. Cl.$^5$ .................... A01N 43/16; C07D 311/92
[52] U.S. Cl. ...................................... 514/455; 549/389
[58] Field of Search .................. 514/455, 454, 453

[56] References Cited

U.S. PATENT DOCUMENTS 3,914,317 10/1975 McGahren .................... 260/592
4,935,363 6/1990 Brown et al. .................... 435/172

OTHER PUBLICATIONS

W. J. McGahren et al., *J. Amer. Chem. Soc.*, 96: 1616–1617 (1974).
W. J. McGahren et al., *J. Org. Chem.*, 41: 66–71 (1976).
K. Fukuyama et al., *Tetrahedron Lett.*, 3: 189–190 (1976).
K. Fukuyama et al., *J.C.S. Perkin II*, 683–686 (1978).
M. S. Brown and J. L. Goldstein, *Science*, 232: 34–47 (1986).
P. T. S. Ma et al., *Proc. Natl. Acad. Sci. USA*, 83: 8370–8374.
J. L. Goldstein and M. S. Brown, *Nature*, 343: 425–430 (1990).

*Primary Examiner*—Carolyn Elmore
*Assistant Examiner*—Brian M. Burn
*Attorney, Agent, or Firm*—Melvin Winokur; Joseph F. DiPrima

[57] ABSTRACT

This invention relates to methods for inhibiting fungal growth employing compounds of formula (I)

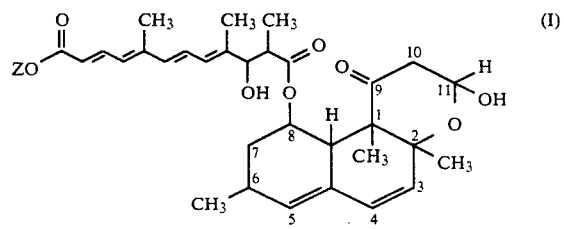

6 Claims, 1 Drawing Sheet

1

ANTIFUNGAL AGENTS

BACKGROUND OF THE INVENTION

This is a continuation-in-part of copending patent application Ser. No. 07/670,638 filed Mar. 18, 1991, now abandoned.

DESCRIPTION OF THE INVENTION

The present invention is directed to novel compounds of structural formula (I) which are useful as inhibitors of fungal growth.

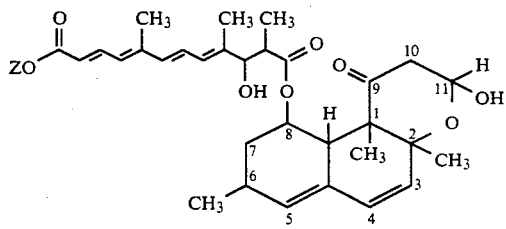

wherein Z is selected from the group consisting of:
a) H;
b) $C_{1-5}$ alkyl;
c) $C_{1-5}$ alkyl substituted with a member of the group consisting of:
  i) phenyl,
  ii) phenyl substituted with methyl, methoxy, halogen (Cl, Br, F, I) or hydroxy; or
a pharmaceutically acceptable salt of a compound of formula (I).

In one embodiment of the present invention are those compounds of formula (I) wherein the relative configuration of the tricyclic ring is as shown below:

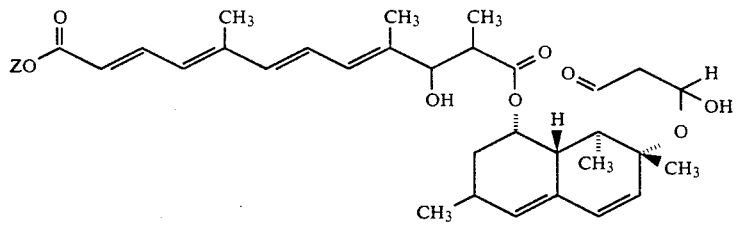

Throughout this specification and claims where stereochemistry is described for the tricyclic ring the configuration implied is relative. The actual configuration may be as shown or that of its enantiomer.

Further illustrating this embodiment are those compounds of structural formula (I) wherein the relative configuration at the 11-position is as shown below:

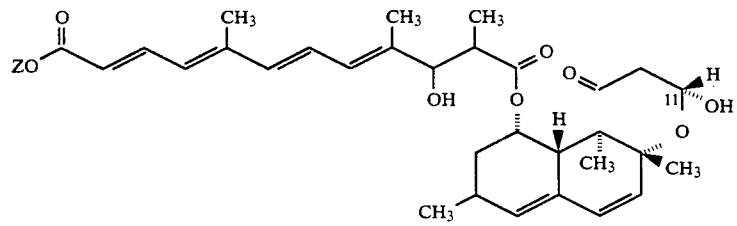

In one class of this embodiment are those compounds of structure (I) wherein the relative configuration at the 6-position is as shown below:

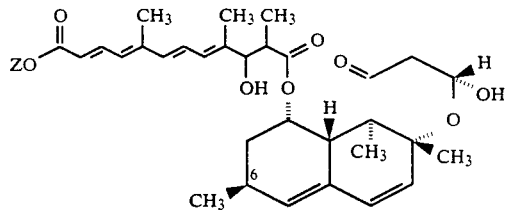

Exemplifying this class is the compound wherein Z is hydrogen or a pharmaceutically acceptable salt thereof. The compound wherein Z is hydrogen is hereafter referred to as Compound A.

Further illustrating this class are those compounds in which Z is $C_{1-5}$ alkyl or $C_{1-5}$ alkyl substituted with phenyl or substituted phenyl wherein the substituent is methyl, methoxy, halogen or hydroxy. In a specific illustration Z is methyl. This compound is hereafter referred to as Compound B.

The compounds of formula (I) are prepared in an aerobic fermentation procedure employing a novel culture, MF2664 identified as *Aspergillus versicolor* (Fungi, Class Hyphomycetes). Although the use of this organism is specifically described herein, other organisms of the genus Aspergillus specifically including mutants of the above described organism are also capable of producing compounds of this invention and are included within this invention.

The culture MF2664 has been deposited, under the Budapest Treaty, with the American Type Culture Collection at 12301 Parklawn Drive, Rockville, Md. 20852 as ATCC 74035. The culture MF2664, identified as a strain of *Aspergillus versicolor* exhibits the following morphological features:

Colonies attaining a diameter of 15 mm on yeast-malt extract agar (Difco) at 20° C. 12/12 hr light/dark in 7 days; no growth on the same medium at 37° C. in 7 days; attaining a diameter of 10 mm on cornmeal agar (Difco) at 20° C.; no growth on cornmeal agar at 37° C. On yeast-malt extract agar, colonies up to 1 mm deep, moderately raised, velutinous to slightly floccose, dull, margin submerged, entire, hyaline to pale greenish yellow, Pale Chalcedony Yellow, Light Chalcedony Yellow (capitalized color names from Ridgway, R. 1912. *Color Standards and Nomenclature*, Washington, D.C.) at the margin, soon dull yellowish green to green, Malachite Green, Light Bice Green, Forest Green, often with mottled appearance due to uneven pigment development in conidial heads, reverse dull yellow gray at the margin, but soon grayish to reddish brown, Isabella Color, Vinaceous Brown, Dark Vinaceous Brown, Hay's Brown, Seal Brown, with similar reddish brown, diffusible pigment exuded from the edges of the colony a few mm into the agar.

Conidiophores arising from a foot cell, 170–500 μm tall, 4.5–7 μm wide, straight to slightly curved or flexuous, sometimes with irregular constrictions, often slightly constricted just below the vesicle, thick-walled, with walls 0.5–1 μm thick, smooth, hyaline to pale gray. Conidial heads 60–180 μm in diameter, biseriate with groups of conidiogenous cells arising from metulae, at first loosely columnar but conidial chains soon splitting to become radiate, a first pale yellow, but soon becoming dull yellowish green to green, often with basal portion remaining pale yellow at maturity, rarely remaining entirely pale yellow at maturity. Conidiogenous cells phialidic, arising from metulae in groups of 1–4, usually 3, 4–7×2–3.5 μm, cylindrical to ampulliform, with distal end tapered to broadly truncate. Metulae broadly cylindrical to clavate, 4.5–7.5×3–4.5 μm. Vesicles 10–15 μm in diameter, subglobose to pyriform, with metulae covering the upper 60–80%. Conidia 2–4.5 μm in diameter, globose to subglobose, minutely echinulate or roughened, hyaline to grayish green in KOH, adhering in chains by colorless connectives. Hyphae septate, smooth, highly branched, often with intercalary or terminal, globose to subglobose cells, up to 10 μm in diameter, sometimes directly giving rise to single or small groups of 3–4 phialidic conidiogenous cells. Huelle cells, sclerotia, and cleistothecia absent.

*Aspergillus versicolor* is a common and widely distributed organism, being reported from arctic to tropical regions from diverse soil types, detritus, plant litter, textiles, food products, animal dung, and living animals. Strain MF2664 can be assigned to Raper and Fennell's *A. versicolor* group (K. B. Raper & D. I. Fennell, The Genus Aspergillus, 1965, Williams & Wilkins, Baltimore) based on the combination of: biseriate conidial heads; relatively long, colorless conidiophores; predominantly dull green pigmentation of the conidia; and lack of Huelle cells and sclerotia. Within the *A. versicolor* group, MF2664 can be distinguished from the other species by the smooth conidiophore walls, relatively small, echinulate conidia, and the dull green conidial heads. According to Raper and Fennell's monograph, *A. versicolor* is highly variable with regard to colony pigmentation, as the specific epithet indicates. The dull yellowish green to green conidial heads of MF2664, along with the dull vinaceous brown reverse and diffusible pigments appear to occupy a central position among the numerous color variants described within this broadly circumscribed species. Likewise, the characteristics of MF2664 agree well with the more modern and succinct species concept of *A. versicolor* presented by Domsch et al., 1980 (Domsch, K. H., W. Gams, T. Anderson, 1980. Compendium of soil fungi. Academic Press, London).

Compounds of this invention can be obtained by culturing an above-noted microorganism on a solid or in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 15 percent by weight. These carbon sources can be used individually in a given medium or several sources in combination in the same medium.

The preferred sources of nitrogen are amino acids such as glycine, methionine, proline, threonine and the like, as well as complex sources such as hydrolyzed proteins, yeast extracts (hydrolysates, autolysates), dried yeast, tomato paste, soybean meal, peptone, corn steep liquor, distillers solubles, malt extracts and the like. Inorganic nitrogen sources such as ammonium salts (e.g. ammonium nitrate, ammonium sulfate, ammonium phosphate, etc.) can also be used, as well as organic sources such as urea. The various sources of nitrogen can be used alone or in combination in amounts ranging between 0.2 to 90 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organisms which serve as seeds in the production of the active compounds. After inoculation, the flasks are incubated with agitation at temperature ranging from 20° to 30° C., preferably 25° to 28° C. Agitation rates may range up to 400 rpm, preferably 140 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 30 days, preferably 4 to 14 days, with or without agitation (depending on whether liquid or solid fermentation media are employed). The fermentation is conducted aerobically at temperatures ranging from 20° to 40° C. If used, agitation may be at a rate to 400 rpm. To obtain optimum results, the temperatures are in the range of 20° to 28° C., most preferably 24° to 26° C. The pH of the nutrient medium suitable for producing the active compounds is in the range of 3.5 to 8.5, most preferably 5.0 to 7.5. After the appropriate period for production of the desired compound, fermentation flasks are harvested and the active compound isolated.

A polar solvent such as an ester, ketone or alcohol may be used to extract a compound of this invention from the solid fermentation medium. A mixture of an ester or ketone and an alcoholic solvent may also be employed.

The mixture is vigorously stirred, filtered, and the filtrate concentrated under reduced pressure. Methanol and water are added to the concentrate, which is then extracted with a water immiscible solvent. The aqueous methanolic layer is removed and evaporated to dryness. The residue is then subjected to several separation steps such as adsorption and chromatography. Fractions are collected and combined after each separation step based on biological assay and/or high performance liquid chromatography (HPLC) analysis.

The preferred solvent for extraction of the solid fermentation is ethyl acetate. After concentration, the preferred partitioning solvent is a 6:4 mixture of hexane and isopropyl acetate.

The chromatographic separations may be carried out using conventional column chromatography. Silica gel is the preferred initial adsorbent. When silica is the adsorbent, an ester/chlorohydrocarbon/organic acid mixture such as ethyl acetate/methylene chloride/acetic acid is useful as an eluant. For reversed phase chromatography the preferred adsorbent is a C-18 bonded phase silica gel. The preferred eluant for reversed phase chromatography is a mixture of acetonitrile and water buffered to a neutral pH with a buffer such as 0.1M phosphate. It is preferable to do the isolation in the absence of light.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The present compounds exhibit broad spectrum antifungal activity as demonstrated by a fungal inhibitory spectrum profile (FISP). The FISP assay employs disc diffusion susceptiblity testing methods to generate a spectrum of activity against a panel of representative yeasts, filamentous fungi and bacteria.

The filamentous fungi used in the assay are Penicillium sp. *Aspergillus niger*, Trichoderma sp., Phoma sp., *Trichoderma lignorum, Fusarium oxysporum, Ustilago maydis, Ceratocystis ulmi, Alternaria soloni, Verticillium serrae, Botrytis allii, Scopulariopsis communis*, Cephalosporium sp., *Cercospora beticola, Rhizomucor miehei, Aspergillus flavus* and *Aspergillus fumigatus*.

The yeasts employed in the assay are *Saccharomyces cerevisiae, Candida albicans, Candida tropicalis, Candida rugosa, Brettanomyces bruxellensis, Torulospora hansenii, Candida guilliermondi, Candida pseudotropicalis, Torulopsis glabrata, Cryptococcus albidus, Cryptococcus laurentii* and *Kluyveromyces fragilis*.

The bacteria employed in the assay are Streptomyces sp., *Acholeplasma laidlawii* and *Bacillus subtilis*.

For carrying out the assay, seeded assay plates are prepared in the following manner according to the type of assay strain.

Inocula for filamentous fungi are prepared by scrapping the surface of stock plates maintained on potato dextrose agar with a moistened sterile dacron swab. The spores and mycelia are then suspended in 10 milliliters of sterile potato dextrose broth and adjusted to 65 percent transmission at 660 nm.

Inocula for yeasts and bacterial strains are prepared from overnight broth cultures which are then diluted into potato dextrose agar to a final concentration of either 40 percent or 70 percent transmission at 660 nm.

When the organism is *Acholephasma laidlawii*, it is suspended in brain heart infusion broth supplemented with 2.5 percent yeast extract and 20 percent heat inactivated horse serum, and the broth adjusted to a final concentration of 60 percent transmission at 660 nm.

For three strains of *Candida albicans* and one strain of *Saccharomyces cerevisiae*, sterile saline is employed in place of potato dextrose broth.

Assay plates for the yeasts and filamentous fungi are prepared by diluting the inoculum into appropriate molten agar medium (45° C.) to obtain a final concentration of 4 percent.

Seeded agar for *Bacillus subtilis* are prepared from a commercially available spore suspension which is diluted directly into molten agar (45° C.) to obtain a final concentration of 0.1 percent.

The seeded agar media thus prepared are dispensed into petri dishes for assays (11 milliliters per dish).

The samples to be tested for production of antifungal agent are applied to 6.2 mm. filter paper discs (25 microliter/disc) and air dried at 24° C. When the sample to be tested is crude broth, it may be centrifuged prior to application. The discs bearing the material to be tested are then applied employing sterile conditions to the seeded assay plates. The assay plates are then incubated at either 28° C. or 37° C. for 24 hours. In one of the assays for *Bacillus subtilis*, the sample is applied to a disc previously impregnated with 4M potassium chloride at 25 μL/disc and then air dried.

Following incubation, the inhibition zones are measured and recorded. The measurements are made from the extreme edge where growth differs from the background zone. The zones are noted as to appearance as fuzzy edge and clear center, hazy throughout, slightly hazy, very hazy or ringed.

The above tests as noted in the FISP profile of Table I demonstrate a broad spectrum of antifungal activity rendering the compounds useful in a wide variety of applications.

The broad spectrum antifungal activity of the present compounds was further determined by broth dilution methods. The compounds are particularly active towards filamentous fungi and yeasts including *Candida albicans* and *Crypt. neoformans*. The sensitivity of filamentous fungi and yeasts was determined using inhibitor dilution assays in microtiter format. A standardized spore suspension for testing the filamentous fungi was prepared by inoculating sterile distilled water with spores such that $1.5-7.5 \times 10^3$ colony forming units were added per well. The microtiter wells were filled with 75 μL of yeast nitrogen base containing 1% Dextrose medium (YNB/D) containing compound. Fifty μL of inoculated YNB/D medium was then added to the wells.

The sensitivity of yeasts was determined by inoculating sterile distilled water with aliquots of a 4-hour yeast culture grown in Yeast Morphology (YM) media at 35° C. and diluting in YNB/D to yield a final concentration of $1.5\text{-}7.5 \times 10^3$ colony forming units/well. Seventy-five μL of inoculated media was added per well. To test the sensitivity of yeast, compound was solubilized in 10 percent aqueous DMSO at 2.56 mg/mL. The compound was diluted serially in YNB/D from 128 to 0.06 μg/mL. The wells were filled with 75 μL of drug containing media. The minimum inhibitory concentration (MIC in μg/mL) is defined as the lowest concentration to prevent growth after an incubation for 48-72 hours, at 35° C. for the filamentous fungi and 24 to 48 hours, at 35° C. for the yeasts. The minimum fungicidal concentration for yeasts in μg/mL is defined as the lowest concentration of drug that totally prevented growth or permitted growth of no more than three colonies from a sample removed from each well and plated on Sabouraud agar media. Representative of the antifungal activity are the minimum inhibitory concentration and minimum fungicidal concentration data shown below in Table II:

TABLE I

| FISP Profile of Compound A (CH$_2$Cl$_2$, 250 μg/mL) | |
|---|---|
| Strain | Zone |
| Filamentous Fungi | |
| *Alternaria solani* | 26F |
| *Aspergillus flavus* | 26H |
| *Aspergillus fumigatus* | 24S |
| *Aspergillus niger* | 0 |
| *Aspergillus niger* | 13H |
| *Botrytis allii* | 20S |
| *Cephalosporium sp.* | 17F |
| *Ceratocystis ulmi* | 10V |
| *Cercospora beticola* | 28S |
| *Fusarium oxysporum* | 14S |
| *Penicillium sp.* | 12H |
| *Penicillium sp.* | 12H |
| *Penicillium sp.* | 11H |
| *Phoma sp.* | 31S |
| *Rhizomucor miehei* | 23H |
| *Scopulariopsis communis* | 15F |
| *Trichoderma lignorum* | 31F |
| *Trichoderma sp.* | 33S |
| *Ustilago maydis* | 12V |
| *Verticillium serrae* | 35S |
| Bacteria | |
| *Streptomyces sp.* | 8V |
| *Acholeplasma laidlawii* | |
| *Bacillus subtilis* | 0 |
| *Bacillus subtilis* - KCl | 0 |
| Yeasts | |
| *Brettanomyces bruxellensis* | 32S |
| *Candida albicans* | 0 |
| *Candida albicans* - YNB | 23V |
| *Candida albicans* | 30S |
| *Candida albicans* | 28S |
| *Candida albicans* | 24S |
| *Candida albicans* | 31S |
| *Candida albicans* - YNB/GLU | 34H |
| *Candida albicans* - YNB/NAG | 35H |
| *Candida guilliermondii* | 0 |
| *Candida pseudotropicalis* | 14V |
| *Candida rugosa* | 30S |
| *Candida tropicalis* | 35S |
| *Cryptococcus albidus* | 11V |
| *Cryptococcus laurentii* | 13H |
| *Cryptococcus laurentii* | 13V |
| *Cryptococcus laurentii* | 11H |
| *Kluyveromyces fragilis* | 12V |
| *Saccharomyces cerevisiae* | 0 |
| *Saccharomyces cerevisiae* | 12H |
| *Saccharomyces cerevisiae* - YNB | 16H |
| *Torulopsis glabrata* | 0 |
| *Torulospora hansenii* | 20H |

FISP data is reported as the diameter (in mm) of the zone of inhibition of growth in agar diffusion assays. The zone is determined by measuring growth that differs from the background lawn. A qualifier is also added to describe the zone quality as listed below: no qualifer: clear zone throughout, sharp edges
F: clear zone, fuzzy edges
S: slightly hazy zone (some growth observed throughout zone)
H: hazy zone (considerable growth observed throughout zone)
V: very hazy zone (zone of inhibition is barely discernable)
R: zone displays a ring of resistant growth

TABLE II

| Minimum Inhibitory and Fungicidal Concentration of Compound A in the Microdilution Broth Assay (MIC/MFC μg/mL) | | |
|---|---|---|
| Fungus | MIC | MFC |
| *Candida albicans* | | |
| MY 1055 | ≦0.06 | ≦0.06 |
| MY 1028 | ≦0.06 | ≦0.06 |
| *Candida tropicalis* | | |
| MY 1012 | ≦0.06 | 0.50 |
| *Candida parapsilosis* | | |
| MY 1010 | 0.25 | 0.25 |
| *Candida guilliermondii* | | |
| MY 1019 | >128 | >128 |
| *Saccharomyces cerevisiae* | | |
| MY 1976 | >128 | >128 |
| *Cryptococcus neoformans* | | |
| MY 1051 | 32 | 32 |
| MY 2061 | 128 | 64 |
| MY 2062 | 64 | 16 |
| MY 1146 | 128 | 64 |
| *Aspergillus fumigatus* | | |
| MF 4839 | 64 | |
| *T. mentagrophytes* | | |
| MF 4864 | 32 | |

Thus the present invention is also directed to a method of treating fungus infections which comprises the administration to an organism in need of such treatment a nontoxic therapeutically effective amount of a compound represented by the structural formula (I) and pharmaceutically acceptable salts thereof. Based on the above MIC data it is determined that generally from 1 to 10 mg/kg should be employed as a unit dosage in an antifungal treatment.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals such as man, or birds or reptiles, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of Formula I.

The following examples illustrate the preparation of the compounds of formula (I) and their incorporation into pharmaceutical compositions and, as such, are not to be considered as limiting the invention set forth in the claims appended hereto.

The composition of media employed in the following Examples are listed below:

| YME Seed Medium | |
|---|---|
| Component | (g/L) |
| Yeast Extract | 4.0 |
| Malt Extract | 10.0 |
| Dextrose | 4.0 |

The medium was prepared with distilled water and the pH adjusted to 7.0 prior to sterilization and sterilized at 121° C. for 20 minutes. The medium was dispensed at 54 mL/250 mL plain Erlenmeyer flask. Cotton closures were used.

NPF-2 PRODUCTION MEDIUM

1. Solid phase:
   Vermiculite: 1250 cc/4 liter roller jar. Latex closure. The vermiculite portion of the medium was sterilized separately for 60 minutes at 121° C.
2. Liquid phase:

| Component | (g/L) |
|---|---|
| Dextrose | 150.0 |
| Urea | 4.0 |
| NZ amine Type A | 4.0 |
| $K_2HPO_4$ | 0.5 |
| $MgSO_4.7H_2O$ | 0.25 |
| KCl | 0.25 |
| $ZnSO_4.7H_2O$ | 0.9 |
| $CaCO_3$ | 16.5 |

The medium was prepared with distilled water (no pH adjustment). The medium was dispensed at 425 mL/1 L Erlenmeyer flask. Cotton closures were used, and the medium was sterilized at 121° C. for 15 minutes.

| KF Seed Medium | | Trace Elements #2 | |
|---|---|---|---|
| Component | g/L | Component | g/L |
| Glucose | 10.0 | $FeSO_4.7H_2O$ | 1.0 |
| Corn Steep Liquor | 5.0 | $MnSO_4.4H_2O$ | 1.0 |
| Tomato Paste | 40.0 | $CuCl_2.2H_2O$ | 0.025 |
| Oat Flour | 10.0 | $CaCl_2$ | 0.1 |
| Trace Elements #2 | 10.0 mL | $H_3BO_3$ | 0.056 |
| Adjust pH = 6.0 | | $(NH_4)_6MoO_2.4H_2O$ | 0.019 |
| | | $ZnSO_4.7H_2O$ | 0.2 |
| | | HCl (Conc) | 5.0 mL |

EXAMPLE 1

Preparation of Compound A

A. Culture and Fermentation i) Preparation of FVM

A lyophilized culture of MF2664 obtained from the Merck Culture Collection was used to prepare frozen vegetative mycelia (FVM) by aseptically transferring the entire contents of the lyophilized preparation into a seed flask (YME, 54 mL/250 mL flask) and incubated at 25° C., 220 rpm for 4 days. The FVM were frozen at −75° C. in 10-15% glycerol. Secondary FVM were prepared from a primary FVM in YME seed medium and frozen as heretofore described.

ii) Seed Culture

Seed cultures of MF2664 *Aspergillus versicolor*, were inoculated with 1.0 mL of the FVM and grown on a gyratory shaker (220 rpm) for 4 days in YME seed (54 mL/250 mL flask) at 25° C. Approximately 10 small sterile ceramic balls and 5 small, sterile ceramic cylinders were added to the flask, which was then incubated on a gyratory shaker for about 2 hours.

iii) Production (one roller jar)

A portion of the seed culture (18 mL) was used to inoculate the liquid portion of a production medium (liquid phase, 425 mL/1 L flask). This mixture was added to a 4 liter vermiculite-containing roller jar (solid phase). The roller jar production vessel was incubated on a roller machine at 25° C. for 13 days.

B. Isolation of Compound A

The contents of fourteen roller bottles of the solid fermentation each prepared as described above in part (A) were combined and extracted twice with a total of 18 L of ethyl acetate. The mixture was then vacuum filtered through Whatman #1 filter paper to remove insolubles. An 830 mg fraction was concentrated by rotary evaporation and subsequently reconstituted in 90% methanol/10% water. This 90% methanol solution was partitioned (1:1) with 6:4 hexane/isopropyl acetate. The methanol/water layer was lyophilized and reconstituted in 4 mL of ethyl acetate/methylene chloride (1:1)+1% acetic acid. This comprised the feed for an 80 mL silica column.

Activity was eluted from the 80 mL silica column using a step gradient beginning with 7:3 methylene chloride/ethyl acetate+1% acetic acid and ending with methanol. The majority of the activity eluted in fractions 8-18, which represented 200 mL of the 1:1 methylene chloride/ethyl acetate+1% acetic acid elution. These fractions were pooled, concentrated to dryness and weighed. The pooled sample which weighed 100 mg, was resuspended in 1.5 mL of methanol. A 0.5 mL aliquot (33 mg) was chromatographed on a Prep-RP-HPLC (Phenomenex ODS 30, 250×22.5, 30:70 acetonitrile 0.01M phosphate buffer pH 7, flow=10 mL/min, UV=320 nm, 10 mL/fraction. The compound A component eluted in fractions 23-26. Buffer was removed from these active fractions by partitioning with one volume of methylene chloride+1% acetic acid. The activity resided in the methylene chloride layer which after evaporation yielded Compound A. Compound A was found to be light sensitive but stable when isolated and worked with in the absence of light.

EXAMPLE 2

Alternate Culture and Production Procedure

A lyophilized culture of MF2664 from the Merck culture collection was placed into 50 mL of KF seed medium in a 250 mL baffled Erlenmeyer flask. This flask was shaken at 220 rpm (2 inch throw New Brunswick shaker) and at 27° C. for 5 days. At the end of this incubation period a 2.5 mL portion of the culture broth was mixed with 0.5 mL of sterile 60% glycerol and portions of this suspension were frozen in six sealed glass vials at −80° C. until use. One of the vials containing MF2664 was thawed to room temperature and was used to inoculate 50 mL of YME seed medium contained in a 250 mL baffled Erlenmeyer flask. This flask was incubated at 25° C., 220 RPM for 3 days. The resulting biomass was aseptically macerated with 12 mm porcelain balls and 24 mL of the slurry was placed into a 425 mL portion of production medium NPF2. The production medium was shaken to disperse the biomass and was added to a 110×535 mm roller culture bottle containing 1250 cc of sterile large-particle vermiculite. The roller culture bottle was shaken well to distribute the contents and was incubated on a roller assembly at 25° C., 75% relative humidity for 18 days.

EXAMPLE 3

As a specific embodiment of an oral composition of a compound of this invention, 200 mg of the compound from Example 1 is formulated with sufficient finely divided lactose to provide a total amount of 580 to 590 mg to fill a size 0 hard gelatin capsule.

EXAMPLE 4

Preparation of an Ammonium Salt

A 0.1 mmol sample of the free acid of a compound of formula (I) is dissolved in 10 mL of ethyl acetate. The resulting solution is saturated with gaseous ammonia upon which the ammonium salt precipitates from solution.

EXAMPLE 5

Preparation of a Potassium Salt

A solution of 0.1 mmol of the free acid of a compound of formula (I) in 10 mL of methanol is treated with an aqueous or methanolic solution containing 0.1 mmol of potassium hydroxide. Evaporation of the solvent affords the potassium salt. In a similar fashion the sodium and lithium salts can be formed.

EXAMPLE 6

Preparation of a Calcium Salt

A solution of 0.1 mmol of the free acid of a compound of formula (I) in 20 mL of 6:4 methanol/water is treated with an aqueous solution of 0.05 mmol of calcium hydroxide. The solvents are evaporated to give the corresponding calcium salt.

EXAMPLE 7

Preparation of an Ethylenediamine Salt

A solution of 0.1 mmol of the free acid of a compound of formula (I) in 10 mL of methanol is treated with 0.05 mmol of ethylenediamine. Evaporation of the solvent affords the ethylenediamine salt.

The procedure can also be applied to the preparation of the N,N''-dibenzylethylenediamine salt.

EXAMPLE 8

Preparation of a Tris(hydroxymethyl)aminomethane Salt

To a solution of 0.1 mmol of the free acid of a compound of formula (I) in 10 mL of methanol is added about 0.1 mmol tris(hydroxymethyl)aminomethane dissolved in 10 mL of methanol. Evaporation of the solvent gives the titled salt. Similarly prepared are the salts of L-ornithine, L-lysine, and N-methylglucamine.

EXAMPLE 9

Preparation of an L-arginine Salt

A solution of 0.1 mmol of the free acid of a compound of formula (I) in 10 mL of 6:4 methanol/water is treated with an aqueous solution of 0.1 mmol of L-arginine. Evaporation of the solvent affords the title salt.

Similarly prepared are the salts of L-ornithine, L-lysine and N-methylglucamine.

EXAMPLE 10

Preparation of a Compound B

One mg of Compound A in 250 μL of methylene chloride was reacted at low temperature with several drops of diazomethane. Seventy-five μg was removed and both samples were immediately concentrated to dryness to quench the reaction. Mass spectral analysis confirmed the presence of the Compound B in the 75 μg sample and $^1$H-NMR confirmed the presence of Compound B in the remaining sample.

EXAMPLE 11

General Method for Preparation of an Ester

A solution of 2 mg of Compound A in 0.5 mL of acetonitrile is treated at room temperature with 2 equivalents of DBU and 2 equivalents of MeI. The reaction is diluted after two hours with 10 mL of dichloromethane and washed successively with 10 mL of 0.1M phosphoric acid, 10 mL of water, 10 mL of saturated sodium bicarbonate and 10 mL of water. After drying over sodium sulfate the organic layer is concentrated and the residue is chromatographed on silica gel using mixtures of dichloromethane and ethyl acetate to give the ester.

The method described above is also suitable for the preparation of other ester derivatives such as ethyl and other lower alkyl esters and benzyl and substituted benzyl esters.

Mass Spectral Data

Mass spectra were acquired on Finnigan-MAT models MAT212 and TSQ70 mass spectrometers. (MATZ212: Electron Impact (EI) mode at 90 eV. Exact mass measurements were performed at high resolution (HR EI) using perfluorokerosene (PFK) as an internal standard. TSQ70: EI mode at 70 eV. Fast Atom Bombardment (FAB) mode employing negative ion detection and ethanolamine as the matrix.)

NMR Spectra

All NMR spectra were acquired on a Varian Unity 500 spectrometer operating at 499.843 MHz for proton measurements and 125.697 MHz for $^{13}$C measurement. Carbon-13 NMR studies and $^1$H NMR studies were performed on a 7 mM solution of Compound A in either $CD_2Cl_2$ or a mixture of 85:15 $CD_3CN/CD_2Cl_2$ at ambient temperature (20°+/−1° C.).

Physical Properties of the compounds of Structure I:
Compound A—the compound of structure I wherein Z is H.

Mass Spectral Data

This compound has the molecular weight 540 by FAB-MS ([M-H]$^-$=539). The molecular formula $C_{31}H_{40}O_8$ was determined by HR EI of the [M-H$_2$O]$^+$ ion: calculated 522.2618, found 522.2623.

$^{13}$C NMR Data in $CD_2Cl_2$ Solution:

Chemical shifts for $^{13}$C spectra recorded in $CD_2Cl_2$ solution are given in ppm relative to tetramethylsilane (TMS) at zero ppm using the solvent peak at 53.8 ppm as an internal standard: 12.3, 13.3, 14.8, 17.8, 21.0, 23.3, 27.3, 35.6, 40.2, 44.1, 47.3, 53.3, 70.2, 78.2, 79.7, 91.9, 119.7, 128.2, 128.3, 128.9, 129.1, 130.4, 130.6, 136.1, 137.0, 140.5, 142.8, 145.7, 171.5, 175.6, 209.1 ppm.

$^{13}$C NMR Data in 85:15 $CD_3CN/CD_2Cl_2$ Solution:

Chemical shifts for $^{13}$C spectra recorded in 85:15 $CD_3CN/CD_2Cl_2$ solution are given in ppm relative to tetramethylsilane (TMS) at zero ppm using the solvent peak of the acetonitrile methyl group at 1.3 ppm as an internal standard: 11.9, 13.2, 14.8, 18.1, 21.1, 23.3, 27.6, 35.8, 40.4, 44.9, 47.8, 54.2, 70.2, 78.0, 80.2, 92.0, 120.9, 128.5, 128.6, 129.2, 129.3, 131.1, 131.5, 136.2, 137.2, 141.3, 141.6, 145.2, 168.0, 175.4, 209.9 ppm.

$^1$H NMR Spectrum (500 MHz) ($CD_2Cl_2$)
See FIG. 1

UV (MeOH) $\mu_{max}$ is at 240 and 340 nm.

IR (as free acid: film on ZnSe) representative peaks 1726, 1709, 1610, 1570, 1455, 1410 cm$^{-1}$.

Compound B—the mono-methyl ester of the compound of structure (I) wherein Z is methyl.

Mass Spectral Data

This compound has the molecular weight of 554 by LR EI analysis.

What is claimed is:

1. A method for inhibiting fungal growth comprising applying to the area where growth is to be controlled an antifungally effective amount of a compound of formula (I):

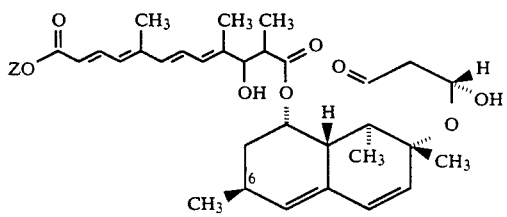

wherein Z is selected from the group consisting of:
a) H;
b) $C_{1-5}$ alkyl; and
c) $C_{1-5}$ alkyl substituted with a member of the group consisting of:
   i) phenyl, and
   ii) phenyl substituted with methyl, methoxy, halogen or hydroxy; or
a pharmaceutically acceptable salt of a compound of formula (I).

2. A method for inhibiting fungal growth in a living organism in need of such treatment comprising the oral, parenteral or systemic administration of an effective amount of a compound of claim 1 to said living organism.

3. A method of claim 2 wherein the living organism is a mammal.

4. A method of claim 2 wherein the living organism is a bird.

5. A method of claim 2 wherein the living organism is a plant.

6. A method of claim 2 wherein the compound is selected from the group consisting of:

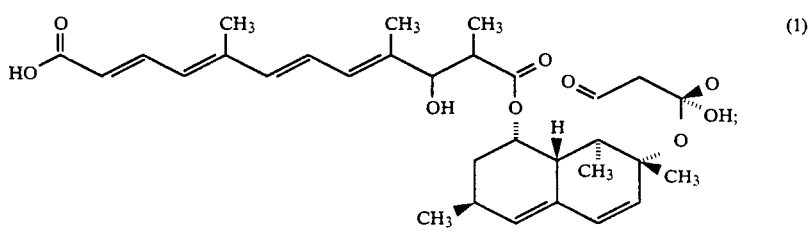

and (2)
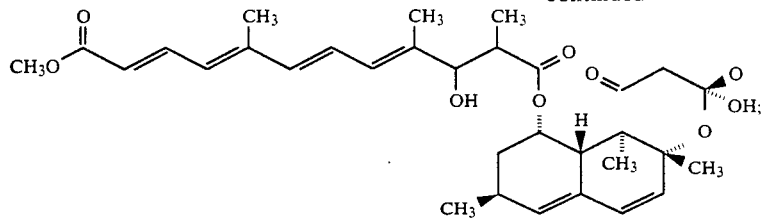
\* \* \* \* \*